United States Patent [19]

Zinnen et al.

[11] Patent Number: 4,642,397
[45] Date of Patent: Feb. 10, 1987

[54] PROCESS FOR SEPARATING ISOMERS OF DINITROTOLUENE

[75] Inventors: Hermann A. Zinnen, Evanston; Thad S. Franczyk, Skokie, both of Ill.

[73] Assignee: UOP Inc., Des Plaines, Ill.

[21] Appl. No.: 782,674

[22] Filed: Oct. 1, 1985

[51] Int. Cl.$^4$ .............................................. C07C 79/10
[52] U.S. Cl. .................................. 568/934; 210/670; 568/932
[58] Field of Search ....................... 208/310 R, 310 Z; 568/934, 932; 585/828–831, 825; 210/660, 670

[56] References Cited

U.S. PATENT DOCUMENTS

| | | | |
|---|---|---|---|
| 2,985,589 | 5/1961 | Broughton et al. | 210/34 |
| 3,069,470 | 12/1962 | Fleck et al. | 260/582 |
| 3,114,782 | 12/1963 | Fleck et al. | 260/674 |
| 3,201,491 | 8/1965 | Stine et al. | 260/676 |
| 3,265,750 | 8/1966 | Peck et al. | 585/825 |
| 3,510,423 | 4/1968 | Neuzil et al. | 585/825 |
| 3,558,730 | 1/1971 | Neuzil | 260/674 |
| 3,558,732 | 1/1971 | Neuzil | 260/674 |
| 3,626,020 | 12/1971 | Neuzil | 260/674 SA |
| 3,663,638 | 5/1972 | Neuzil | 260/674 SA |
| 3,668,267 | 6/1972 | Hedge | 260/674 SA |
| 3,734,974 | 5/1973 | Neuzil | 585/831 |
| 3,864,416 | 2/1975 | Campbell et al. | 585/828 |
| 4,270,013 | 5/1981 | Priegnitz et al. | 568/940 |
| 4,467,126 | 8/1984 | Zinnen | 568/937 |
| 4,480,129 | 10/1984 | Priegnitz et al. | 564/424 |

FOREIGN PATENT DOCUMENTS 149230 11/1980 Japan .

Primary Examiner—Stephen J. Lechert, Jr.
Assistant Examiner—Anne Brookes
Attorney, Agent, or Firm—Thomas K. McBride; John F. Spears, Jr.; Jack H. Hall

[57] ABSTRACT

This invention comprises a process for separating 2,4-dinitrotoluene from a feed mixture comprising 2,4-dinitrotoluene and at least one isomer thereof, which process comprises contacting the mixture at adsorption conditions with an adsorbent comprising an X or Y type zeolite cation exchanged with a cation in the group K, Na, Ca, Ba, Li or Mg, thereby selectively adsorbing the 2,4-dinitrotoluene. The remainder of the feed mixture is removed from the adsorbent and the 2,4-dinitrotoluene is recovered by desorption at desorption conditions with a desorbent material comprising a $C_3$ to $C_5$ alcohol, a ketone, toluene, an ester or a nitrocompound.

12 Claims, 13 Drawing Figures

PROCESS FOR SEPARATING ISOMERS OF DINITROTOLUENE

BACKGROUND OF THE INVENTION

1. Field of the Invention

The field of art to which this invention pertains is the solid bed adsorptive separation of isomeric dinitrotoluenes. More specifically, the invention relates to a process for separating 2,4-dinitrotoluene from the other dinitrotoluene isomers by employing a solid bed adsorption system.

2. Background Information

The isomers, 2,4-dinitrotoluene and 2,6-dinitrotoluene are important starting materials for making polyurethanes which are useful in many applications as rigid or flexible forms or as fibers, e.g., insulation, soundproofing, interlinings for clothing and sleeping bags, cushions, spandex, etc.

It is common industrial practice to make polyurethane from a mixture of the isomers, 2,4- and 2,6-toluene diisocyanate (TDI), for example 80/20 or 65/35, derived from 2,4- and 2,6-dinitrotoluene, because it is difficult and expensive to separate them by existing techniques. Current methods of separating the isomers involve crystallization, e.g. U.S. Pat. No. 4,246,187, and hence, are energy-intensive and time-consuming. Moreover, polyurethanes derived from pure 2,4-dinitrotoluene have dramatically different properties compared to materials synthesized from mixtures. It is further expected that polyurethanes synthesized from (relatively) pure 2,6-dinitrotoluene will have different and more useful properties, for example, a higher glass transition temperature, Tg, and greater stability. Also, the reaction speed with a single isomer is expected to be more consistent. Accordingly, it is desirable to separate the TDI isomers or their precursors, the dinitrotoluenes, by an economical process.

It is well known in the separation art that certain crystalline aluminosilicates can be used to separate hydrocarbon types from mixtures thereof. Furthermore, X and Y zeolites have been employed in a number of processes to separate individual hydrocarbon isomers.

It is known from U.S. Pat. No. 3,069,470 to Fleck et al, to use type X zeolites for the separation of the meta isomer from other isomers of toluidine. From U.S. Pat. No. 4,480,129, it is known that X and Y type zeolites, exchanged with transition metals, are paraselective in a mixture of isomers of toluidine. In Ser. No. 537,123 owned by the present assignee, it is disclosed to separate p-toluidine from its isomers with an X- or Y-type zeolite exchanged with Fe, Mn, Co, Ni or Zn and a desorbent comprising aniline or, when using an X-type zeolite, alkylamine having greater than eight carbons.

In Japanese Patent Application No. 56905/79, publicly disclosed on Nov. 20, 1980, it is disclosed that a solid adsorbent containing titanium oxide will selectively adsorb the p-isomer of toluidine.

It is known from U.S. Pat. No. 4,270,013 to Priegnitz et al that ortho-nitrotoluene may be separated from other nitrotoluene isomers by using a type X zeolite containing at exchangeable cationic sites one cation selected from a group that includes potassium and barium. The specific desorbent materials disclosed by this reference are toluene and 1-hexanol. The separation of isomers of disubstituted benzenes with crystalline aluminosilicates having silica/alumina mole ratio of at least 12 is disclosed in U.S. Pat. No. 4,467,126 to Zinnen.

SUMMARY OF THE INVENTION

In brief summary, the invention is, in one embodiment, a process for separating 2,4-dinitrotoluene from a mixture comprising 2,4-dinitrotoluene and at least one isomer thereof, such as 2,6-dinitrotoluene. The process comprises contacting the mixture at adsorption conditions with an adsorbent comprising an L, X or Y-type zeolite cation exchanged with a cation in the group Ba, Ca, Na, K, Li or Mg, thereby selectively adsorbing the 2,4-dinitrotoluene thereon. The remainder of the feed mixture is then removed from the adsorbent and the 2,4-dinitrotoluene recovered by desorption at desorption conditions with a desorbent material comprising a $C_3$ to $C_5$ alcohol, a ketone, an ester or a nitrocompound.

Other embodiments of our invention encompass details about feed mixtures, adsorbents, desorbent materials and operating conditions, all of which are hereinafter disclosed in the following discussion of each of the facets of the present invention.

DESCRIPTION OF THE INVENTION

Figure 1:
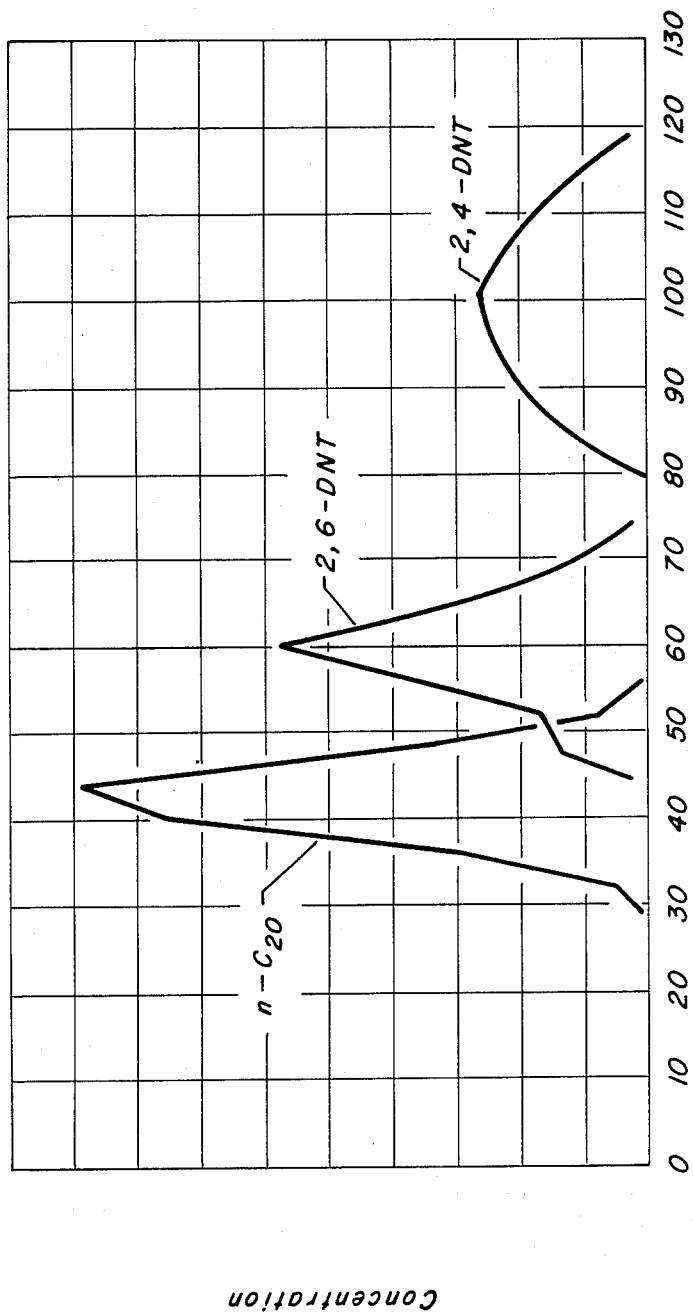
FIGS. 1–FIGS. 13 represent the result of a chromatographic analysis of the effluent of pulse test conducted in Examples 2 and 3 showing the separation of the isomers of dinitrotoluene by various adsorbent and desorbent combinations of the invention.
Figure 2:
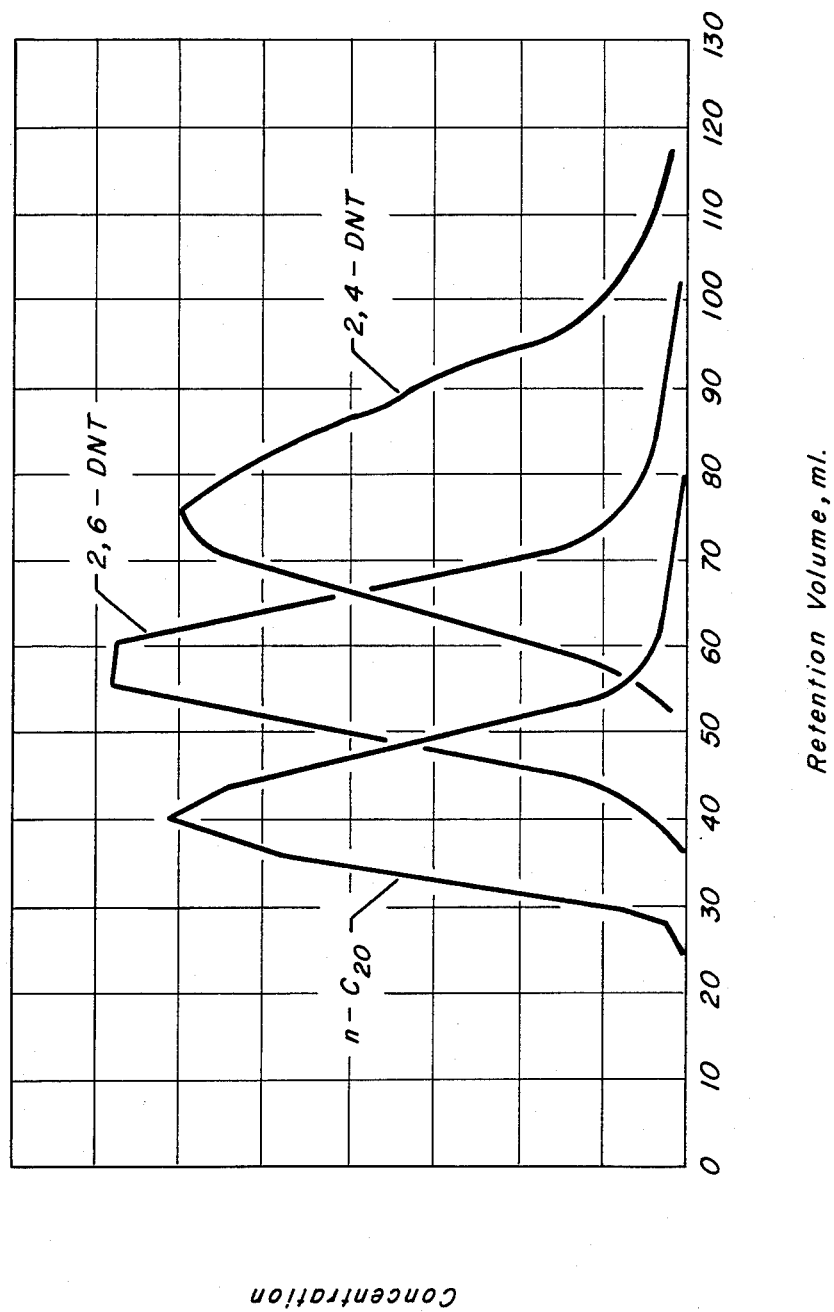
Figure 3:
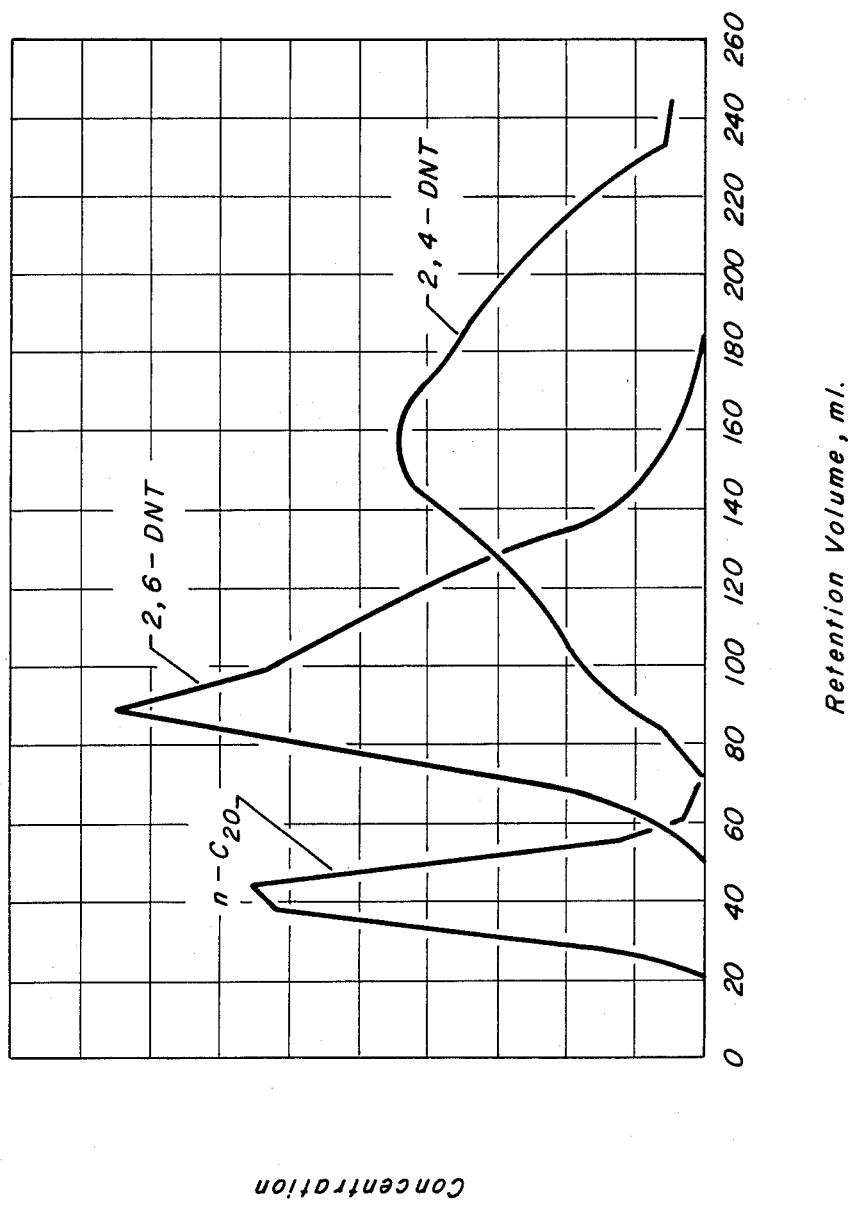
Figure 4:
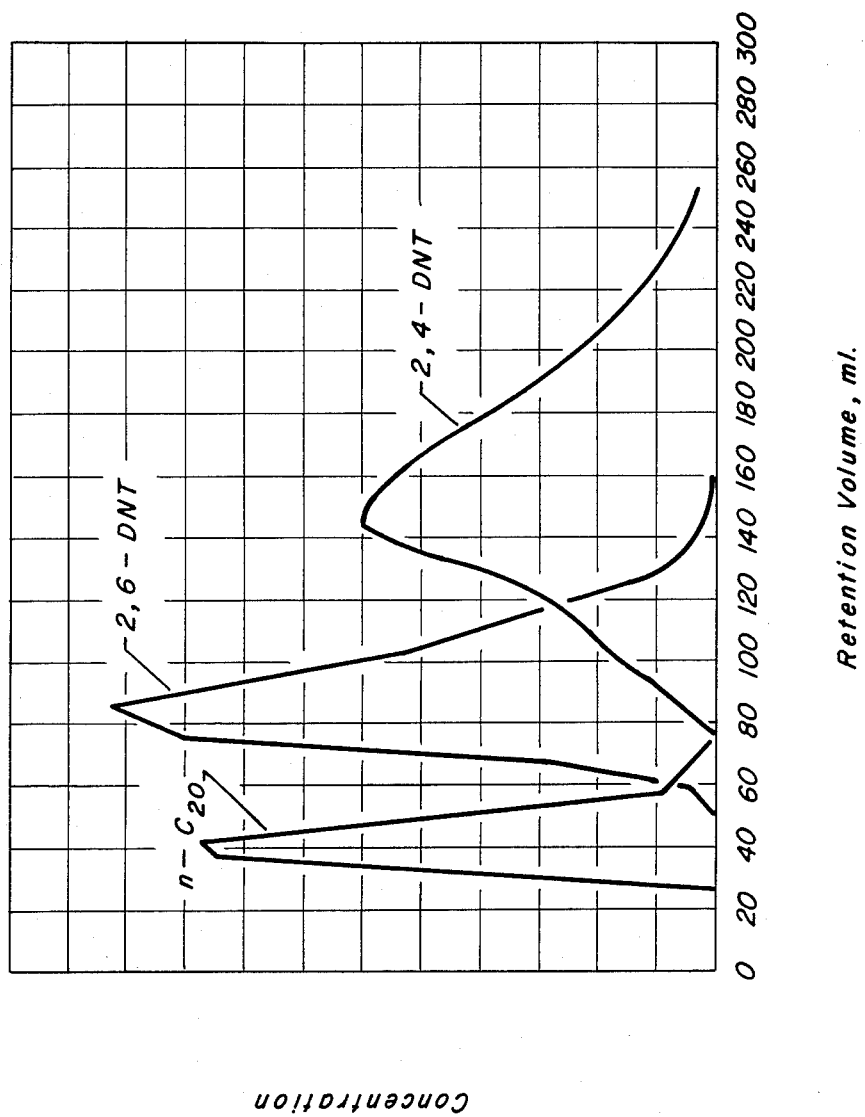
Figure 5:
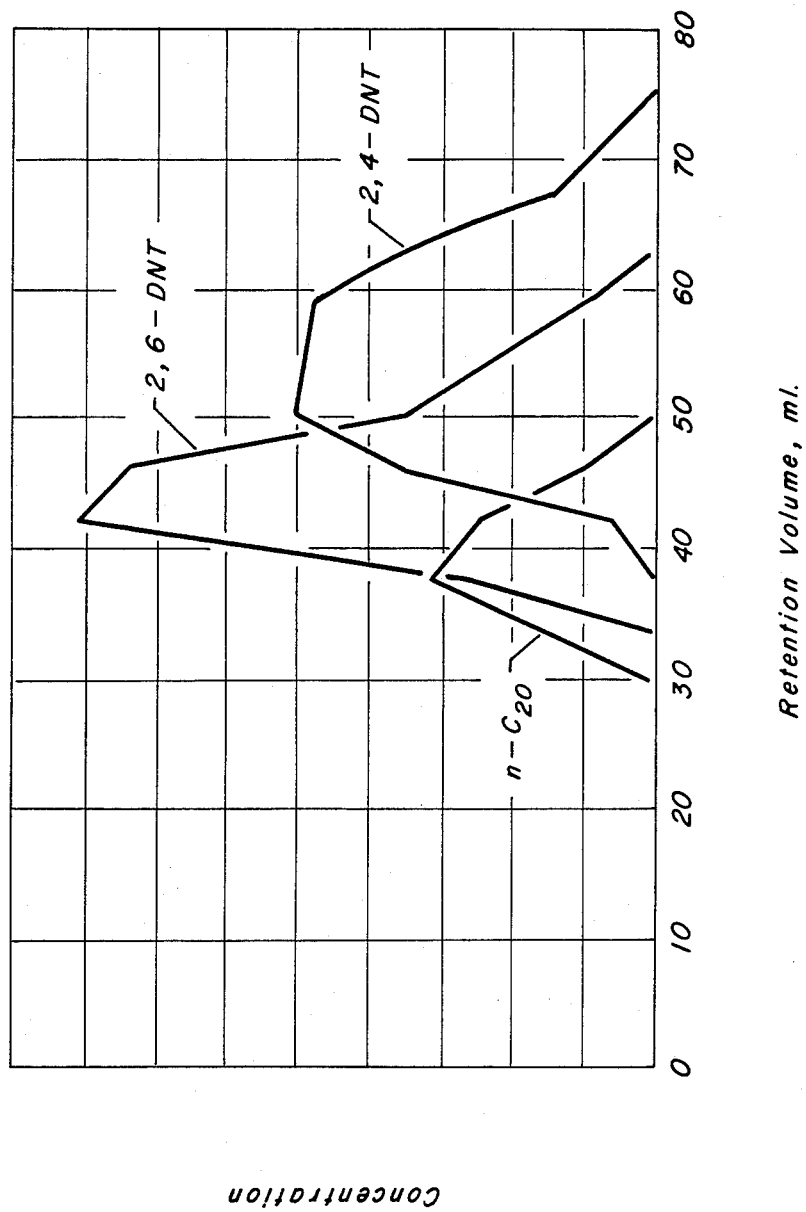
Figure 6:
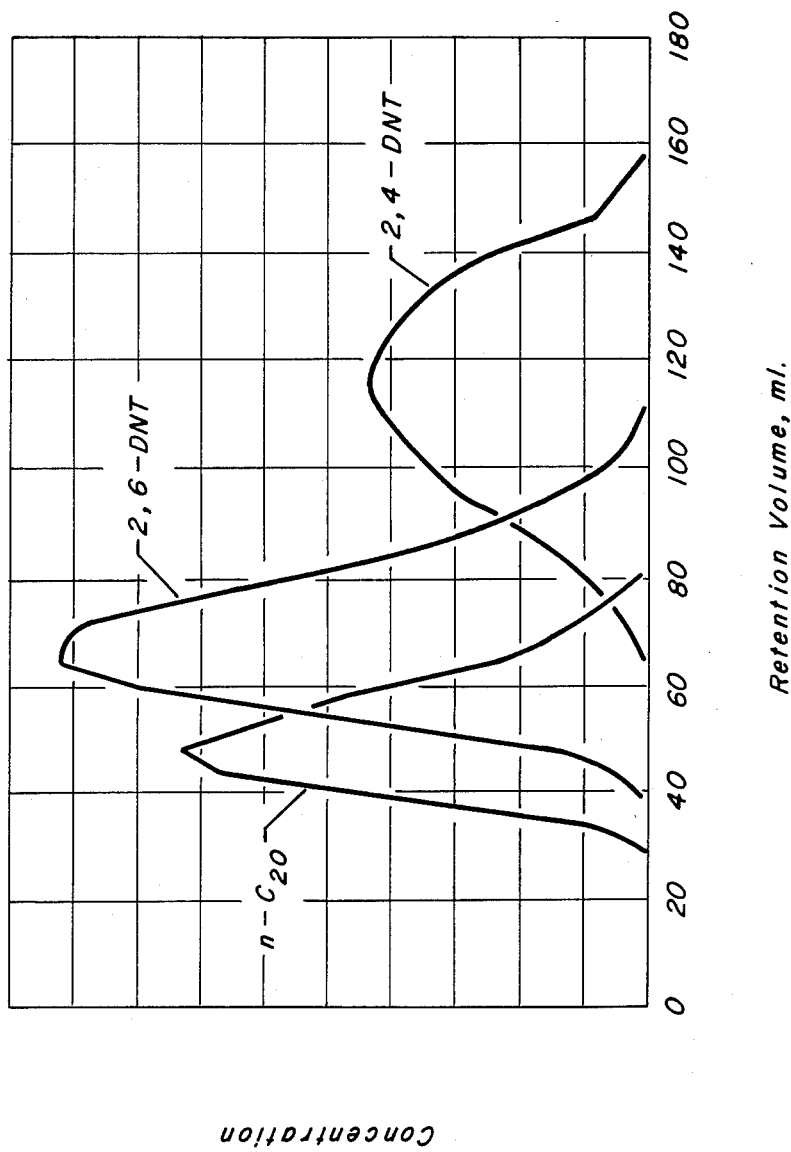
Figure 7:
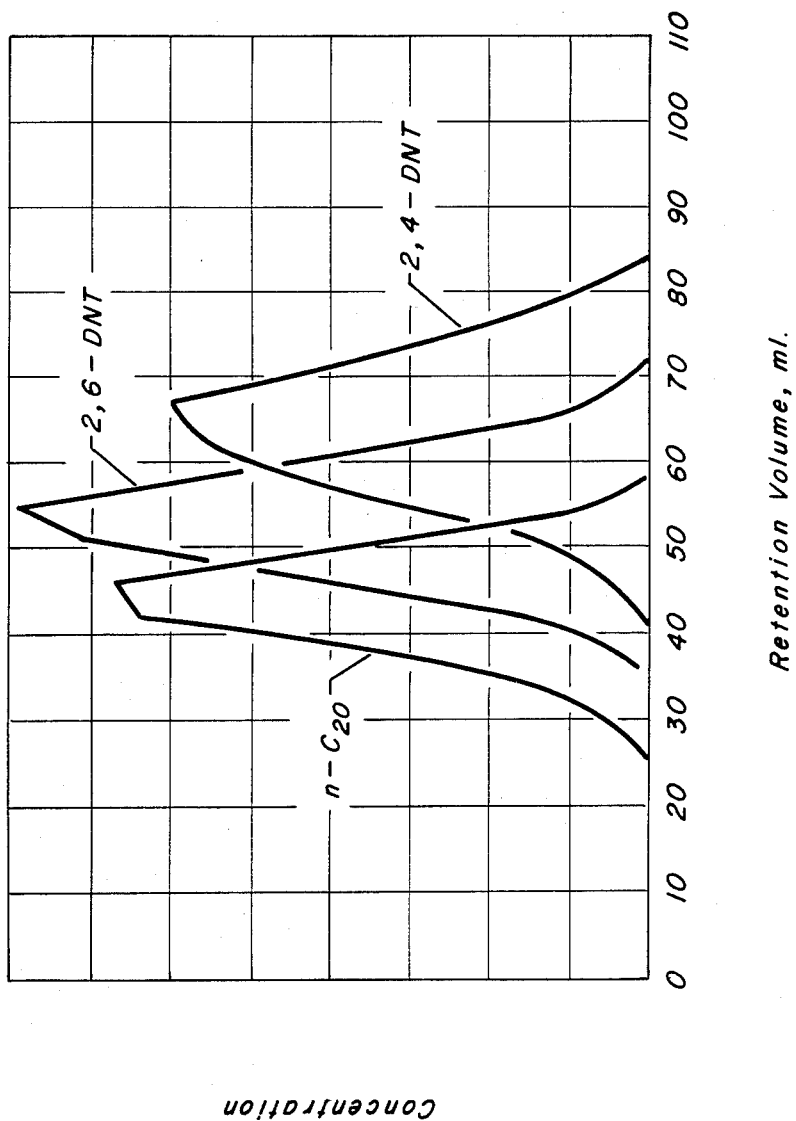
Figure 8:
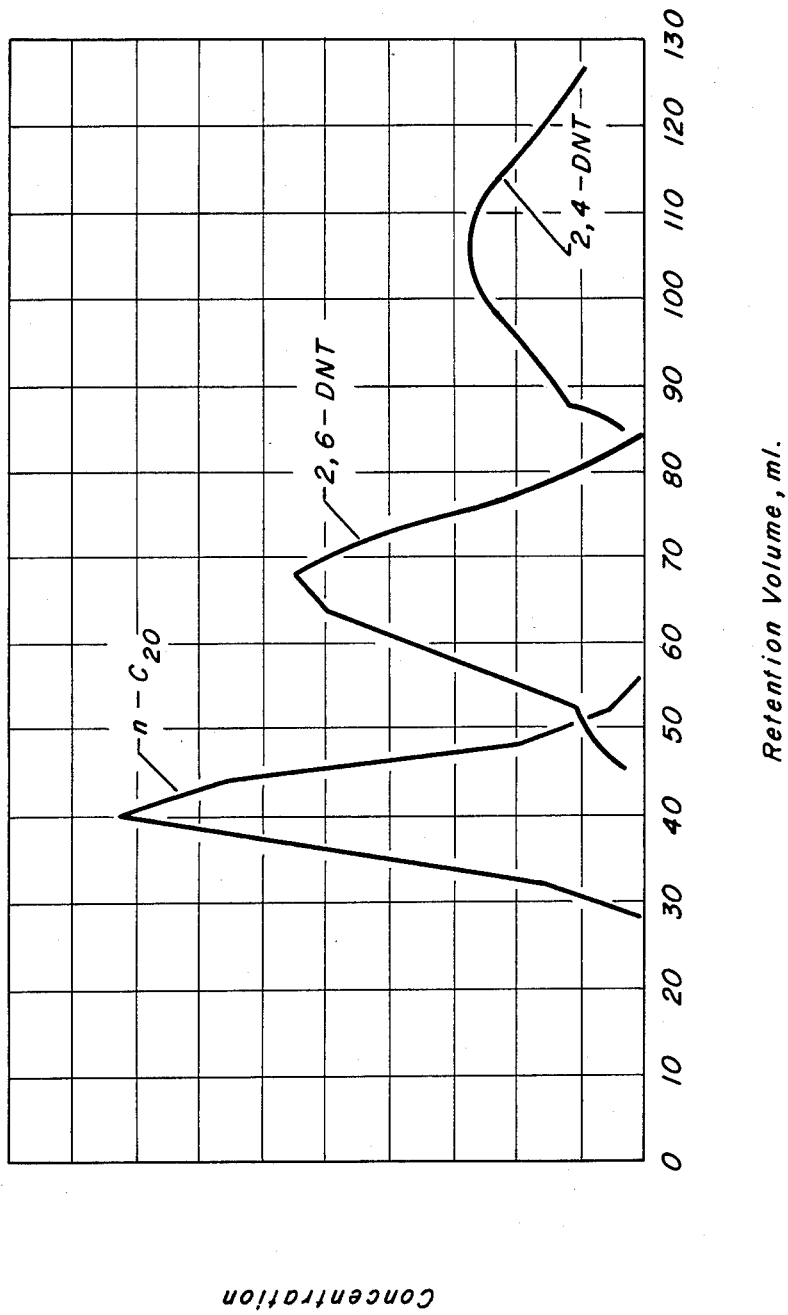
Figure 9:
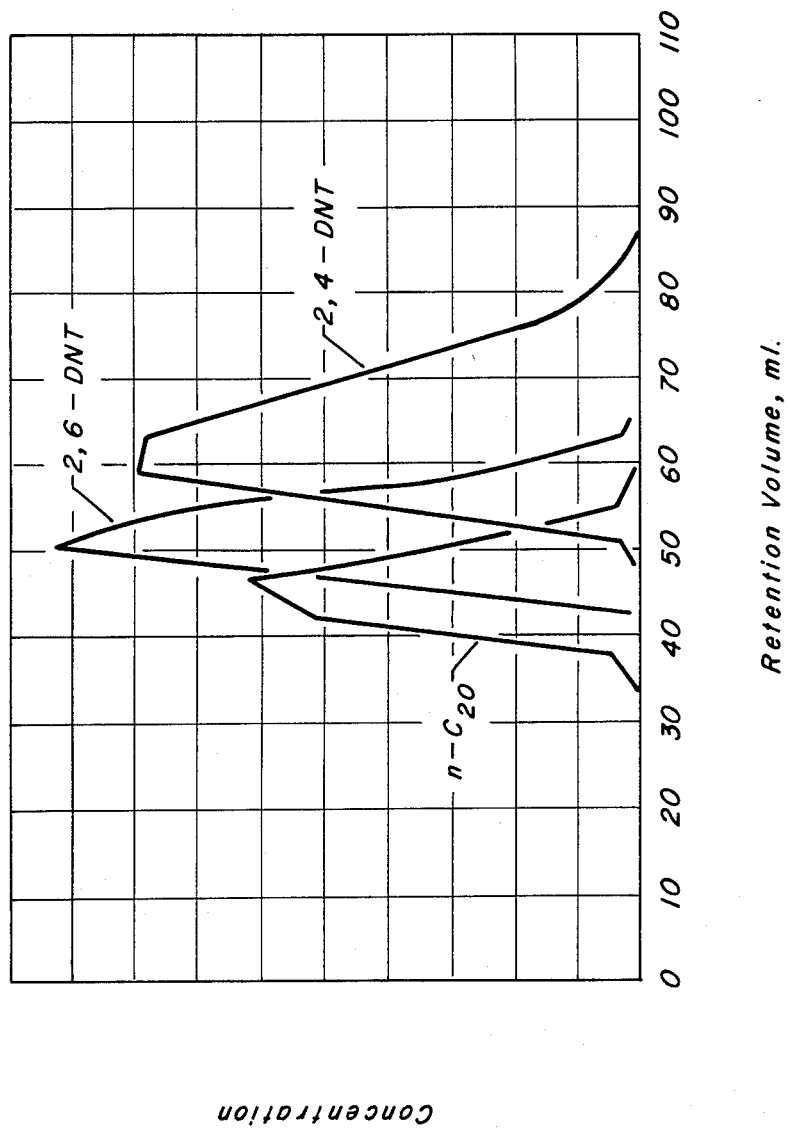

At the outset, the definitions of various terms used throughout the specification will be useful in making clear the operation, objects and advantages of our process.

A "feed mixture" is a mixture containing one or more extract components and one or more raffinate components to be separated by our process. The term "feed stream" indicates a stream of a feed mixture which passes to the adsorbent used in the process.

An "extract component" is a compound or type of compound that is more selectively adsorbed by the adsorbent while a "raffinate component" is a compound or type of compound that is less selectively adsorbed. In this process, 2,4-dinitrotoluene is an extract component and 2,6-dinitrotoluene and, if present, 2,3- and 3,4-dinitrotoluene are raffinate components. The term "desorbent material" shall mean generally a material capable of desorbing an extract component. The term "desorbent stream" or "desorbent input stream" indicates the stream through which desorbent material passes to the adsorbent. The term "raffinate stream" or "raffinate output stream" means a stream through which a raffinate component is removed from the adsorbent. The composition of the raffinate stream can vary from essentially 100% desorbent material to essentially 100% raffinate components. The "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. At least a portion of the extract stream and preferably at least a portion of the raffinate stream from the separation process are passed to separation means, typically fractionators, where at least a portion of the desorbent material is separated to produce an extract product and a raffinate product. The terms "extract product" and "raffinate product" mean products produced by the process containing, respectively, an extract component and a raffinate component in higher concentrations than those found in the extract stream and the raffinate stream. Although it is possible by the process of this invention to produce a high purity product at high recoveries, it will be appreciated that an extract component is never completely adsorbed by the adsorbent, nor is a raffinate component completely nonadsorbed by the adsorbent. Therefore, varying amounts of a raffinate component can appear in the extract stream and, likewise, varying amounts of an extract component can appear in the raffinate stream. The extract and raffinate streams then are further distinguished from each other and from the feed mixture by the ratio of the concentrations of an extract component and a raffinate component appearing in the particular stream. More specifically, the ratio of the concentration of 2,4-dinitrotoluene to that of a less selectively adsorbed isomer, 2,6-dinitrotoluene, will be lowest in the raffinate stream, next highest in the feed mixture, and the highest in the extract stream. Likewise, the ratio of the concentration of less selectively adsorbed 2,6-dinitrotoluene to that of more selectively adsorbed 2,4-dinitrotoluene will be highest in the raffinate stream, next highest in the feed mixture, and the lowest in the extract stream.

The term "selective pore volume" of the adsorbent is defined as the volume of the adsorbent which selectively adsorbs an extract component from the feed mixture. The term "non-selective void volume" of the adsorbent is the volume of the adsorbent which does not selectively retain an extract component from the feed mixture. This volume includes the cavities of the adsorbent which contain no adsorptive sites and the interstitial void spaces between adsorbent particles. The selective pore volume and non-selective void volume are generally expressed in volumetric quantities and are of importance in determining the proper flow rates of fluid required to be passed into an operational zone for efficient operations to take place for a given quantity of adsorbent. When adsorbent "passes" into the operational zone employed in one embodiment of this process, its non-selective void volume together with its selective pore volume carries fluid into that zone. The non-selective void volume is utilized in determining the amount of fluid which should pass into the same zone in a countercurrent direction to the adsorbent to displace the fluid present in the non-selective void volume. If the fluid flow rate passing into a zone is smaller than the non-selective void volume rate of adsorbent material passing into that zone, there is a net entrainment of liquid into the zone by the adsorbent. Since this net entrainment is a fluid present in the non-selective void volume of the adsorbent, it in most instances comprises less selectively retained feed components. The selective pore volume of an adsorbent can in certain instances adsorb portions of raffinate material from the fluid surrounding the adsorbent since in certain instances there is competition between extract material and raffinate material for adsorptive sites within the selective pore volume. If a large quantity of raffinate material with respect to extract material surrounds the adsorbent, raffinate material can be competitive enough to be adsorbed by the adsorbent.

The prior art has recognized that certain characteristics of adsorbents are highly desirable, if not absolutely necessary, to the successful operation of a selective adsorption process. Such characteristics are equally important to this process. Among such characteristics are: adsorptive capacity for some volume of an extract component per volume of adsorbent; the selective adsorption of an extract component with respect to a raffinate component and the desorbent material; and sufficiently fast rates of adsorption and desorption of an extract component to and from the adsorbent. Capacity of the adsorbent for adsorbing a specific volume of an extract component is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate an extract component of known concentration contained in a particular charge rate of feed mixture. A reduction in the amount of adsorbent required for a specific adsorptive separation reduces the cost of a separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possess adsorptive selectivity, (B), for one component as compared to another component. Relative selectivity can be expressed not only for one feed component as compared to another but can also be expressed between any feed mixture component and the desorbent material. The selectivity, (B), is defined as the ratio of the two components of the adsorbed phase over the ratio of the same two components in the unadsorbed phase at equilibrium conditions. Relative selectivity is shown as Equation 1, below:

$$\text{Selectivity} = (B) = \frac{[\text{vol. percent } C/\text{vol. percent } D]_A}{[\text{vol. percent } C/\text{vol. percent } D]_U} \quad \text{Equation 1}$$

where C and D are two components of the feed represented in volume percent and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases. Where selectivity of two components approaches 1.0, there is no preferential adsorption of one component by the adsorbent with respect to the other; they are both adsorbed (or non-adsorbed) to about the same degree with respect to each other. As the (B) becomes less than or greater than 1.0, there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D.

The third important characteristic is the rate of exchange of the extract component of the feed mixture material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

Adsorbents to be used in the process of this invention will comprise specific crystalline aluminosilicates. Particular crystalline aluminosilicates encompassed by the present invention include crystalline aluminosilicate cage structures in which the alumina and silica tetrahedra are intimately connected in an open three dimensional network to form cage-like structures with window-like pores of about 8 Å free diameter. The tetrahedra are crosslinked by the sharing of oxygen atoms with spaces between the tetrahedra occupied by water molecules prior to partial or total dehydration of this zeolite. The dehydration of the zeolite results in crystals interlaced with cells having molecular dimensions and thus the crystalline aluminosilicates are often referred to as "molecular sieves," particuarly when the separation which they effect is dependent essentially upon differences between the sizes of the feed molecules as, for instance, when smaller normal paraffin molecules are separated from larger isoparaffin molecules by using a particular molecular sieve.

In hydrated form, the crystalline aluminosilicates used in the process of this invention generally encompass those zeolites represented by the Formula 1 below:

$M_{2/n}O:Al_2O_3:wSiO_2:yH_2:yH_2O$     Formula 1 where "M" is a cation which balances the electrovalence of the aluminum-centered tetrahedra and which is generally referred to as an exchangeable cationic site, "n" represents the valence of the cation, "w" represents the moles of $SiO_2$, and "y" represents the moles of water. The generalized cation "M" may be monovalent, divalent or trivalent or mixtures thereof.

The prior art has generally recognized that adsorbents comprising L, X and Y zeolites can be used in certain adsorptive separation processes. These zeolites are described and defined in U.S. Pat. Nos. 3,216,789, 2,882,244 and 3,130,007, respectively, incorporated herein by reference thereto. The X zeolite in the hydrated or partially hydrated form can be represented in terms of mole oxides as shown in Formula 2 below:

$(0.9\pm0.2)M_{2/n}O:Al_2O_3:(2.5\pm0.5)SiO_2:yH_2O$     Formula 2 where "M" represents at least one cation having a valence of not more than 3, "n" represents the valence of "M", and "y" is a value up to about 9 depending upon the identity of "M" and the degree of hydration of the crystal. As noted from Formula 2, the $SiO_2/Al_2O_3$ mole ratio of X zeolite is 2.5±0.5. The cation "M" may be one or more of a number of cations such as a hydrogen cation, an alkali metal cation, or an alkaline earth cation, or other selected cations, and is generally referred to as an exchangeable cationic site. As the X zeolite is initially prepared, the cation "M" is usually predominately sodium, that is, the major cation at the exchangeable cationic sites is sodium and the zeolite is therefore referred to as a sodium-X zeolite. Depending upon the purity of the reactants used to make the zeolite, other cations mentioned above may be present, however, as impurities. The Y zeolite in the hydrated or partially hydrated form can be similarly represented in the terms of mole oxides as in Formula 3 below:

$(0.9\pm0.2)M_{2/n}O:Al_2O_3:wSiO_2:yH_2O$     Formula 3 where "M" is at least one cation having a valence not more than 3, "n" represents the valence of "M", "w" is a value greater than about 3 up to about 6, and "y" is a value up to about 9 depending upon the identity of "M" and the degree of hydration of the crystal. The $SiO_2/Al_2O_3$ mole ratio for Y zeolites can thus be from about 3 to about 6. Like the X zeolite, the cation "M" may be one or more of a variety of cations but, as the Y zeolite is initially prepared, the cation "M" is also usually predominately sodium. A Y zeolite containing predominately sodium cations at the exchangeable cationic sites is therefore referred to as a sodium-Y zeolite.

The L zeolite in the hydrated or partially hydrated form may be represented in terms of mole oxides as in Formula 4 below:

$0.9-1.3M_{2/n}O:Al_2O_3:5.2-6.9SiO_2:yH_2O$     Formula 4 where M designates at least one exchangeable cation as referred to above, n is the valence of metal, M and y may be any value from 0 to about 9. It is preferred to synthesize the potassium form of the L-type zeolite since the reactants to make this form are readily available and generally water soluble. Thus the as-made form of the L-zeolite is referred to as potassium-L, or K-L, zeolite. L-zeolite is characterized by planar 12-ring pores aligned to produce one-dimensional channels, linked to each other by small pore openings which will not admit water molecules. A minor two-dimensional pore system also exists, parallel to the aforesaid channels.

Cations occupying exchangeable cationic sites in the zeolite may be replaced with other cations by ion exchange methods well-known to those having ordinary skill in the field of crystalline aluminosilicates. Such methods are generally performed by contacting the zeolite or an adsorbent material containing the zeolite with an aqueous solution of the soluble salt of the cation or cations desired to be placed upon the zeolite. After the desired degree of exchange takes place, the sieves are removed from the aqueous solution, washed, and dried to a desired water content. By such methods the sodium cations and any non-sodium cations which might be occupying exchangeable sites as impurities in a sodium X or sodium-Y zeolite can be partially or essentially completely replaced with other cations. The zeolite used in the process of this invention contains cations at exchangeable cationic sites selected from the group of metals K, Na, Ca, Ba, Li or Mg. Preferred zeolites are the Y-type whose exchangeable ions have been exchanged with K and Ca.

Typically, adsorbents used in separative processes contain zeolite crystals dispersed in an amorphous material or inorganic matrix. The zeolite will typically be present in the adsorbent in amounts ranging from about 75 to about 98 wt. % based on volatile-free composition. Volatile-free compositions are generally determined after the adsorbent has been calcined at 900° C. in order to drive off all volatile matter. The remainder of the adsorbent will generally be the inorganic matrix material such as silica, titania, or alumina or mixtures thereof, or compounds, such as clays, which material is present in intimate mixture with the small particles of the zeolite material. This matrix material may be an adjunct of the manufacturing process for zeolite (for example, intentionally incomplete purification of either zeolite during its manufacture) or it may be added to relatively pure zeolite, but in either case its usual purpose is as a binder to aid in forming or agglomerating the hard crystalline particles of the zeolite. Normally, the adsorbent will be in the form of particles such as extrudates, aggregates, tablets, macrospheres or granules having a desired particle size range. The typical adsorbent will have a particle size range of about 16–60 mesh (Standard U.S. Mesh). Examples of zeolites used in adsorbents known to the art, either as is or after cation exchange, are "Molecular Sieves 13X" and "SK-40" both of which are avilable from the Linde Company, Tonawanda, N.Y. The first material contains X zeolite while the latter material contains Y zeolite.

Ideally, desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While separation of an extract component from a raffinate componet is theoretically possible when the selectivity of the adsorbent for the extract component with respect to the raffinate component is just slightly greater than 1.0, it is preferred that such selectivity be reasonably greater than 1.0. Like relative volatility, the higher the selectivity, the easier the separation is to perform. Higher selectivities permit a smaller amount of adsorbent to be used.

Desorbent materials used in various prior art adsorptive separation processes vary depending upon such factors as the type of operation employed. In the swing bed system in which the selectively adsorbed feed component is removed from the adsorbent by a purge stream desorbent, selection is not as critical and desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent. However, in adsorptive separation processes which are generally operated continuously at substantially constant pressures and temperatures to insure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity (hereafter discussed in more detail), it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for an extract component with respect to a raffinate component. Desorbent materials should additionally be substances which are easily separable from the feed mixture that is passed into the process. Both the raffinate stream and the extract stream are removed from the adsorbent in admixture with desorbent material and without a method of separating at least a portion of the desorbent material, the purity of the extract product and the raffinate product would not be very high nor would the desorbent material be available for reuse in the process. It is therefore contemplated that any desorbent material used in this process will preferably have a substantially different average boiling point than that of the feed mixture to allow separation of at least a portion of desorbent material from feed components in the extract and raffinate streams by simple fractional distillation, thereby permitting reuse of desorbent material in the process. The term "substantially different" as used herein shall mean that the difference between the average boiling points between the desorbent material and the feed mixture shall be at least about 5° C. The boiling range of the desorbent material may be higher or lower than that of the feed mixture. Finally, desorbent materials should also be materials which are readily available and therefore reasonable in cost. In the preferred isothermal, isobaric, liquid-phase operation of the process of our invention, we have found that desorbent material comprising a $C_3$ to $C_5$ alcohol, e.g., propanol, butanol and pentanol, a ketone, e.g., methyl ethyl ketone, diethyl ketone, 2-heptanone, etc., esters, e.g., n-propyl acetate and ethyl acetate etc., nitrocompounds, e.g., nitrobenzene, etc. will result in selectivity for the 2,4-dinitrotoluene isomer when used with the above discussed adsorbents. The $C_3$ to $C_5$ alcohols and ethyl acetate are the most preferred desorbents in this process, especially in combination with toluene, which acts as a diluent for the desorbent.

Certain combinations of adsorbent and desorbent were found to be most effective in separating the DNT isomers and therefore, the most preferred adsorbent-desorbent combinations are K-L zeolite with butanol desorbent, K-Y zeolite with butanol or ethyl acetate and Ca-Y zeolite with pentanol desorbent. Each of these combinations exhibited, in the pulse tests, good selectivity and resolution and well-shaped elution profiles. Furthermore, these desorbents are inexpensive, available chemicals, having low boiling points with respect to the DNT isomers.

The adsorbent may be employed in the form of a dense compact fixed bed which is alternatively contacted with the feed mixture and desorbent materials. In the simplest embodiment of the invention, the adsorbent is employed in the form of a single static bed in which case the process is only semi-continuous. In another embodiment, a set of two or more static beds may be employed in fixed bed contacting with appropriate valving so that the feed mixture is passed through one or more adsorbent beds while the desorbent materials can be passed through one or more of the other beds in the set. The flow of feed mixture and desorbent materials may be either up or down through the desorbent. Any of the conventional apparatus employed in static bed fluid-solid contacting may be used.

Moving bed or simulated moving bed flow systems, however, have a much greater separation efficiency than fixed bed systems and are therefore preferred. In the moving bed or simulated moving bed processes, the retention and displacement operations are continuously taking place which allows both continuous production of an extract and a raffinate stream and the continual use of feed and displacement fluid streams. One preferred embodiment of this process utilizes what is known in the art as the simulated moving bed countercurrent flow system. The operating principles and sequence of such a flow system are described in U.S. Pat. No. 2,985,589, incorporated herein by reference. In such a system, it is the progressive movement of multiple liquid access points down a molecular sieve chamber that simulates the upward movement of molecular sieve contained in the chamber. Reference can also be made to D. B. Broughton's U.S. Pat. No. 2,985,589 and to a paper entitled, "Continuous Adsorptive Processing—A New Separation Technique" by D. B. Broughton presented at the 34th Annual Meeting of the Society of Chemical Engineers at Tokyo, Japan on Apr. 2, 1969, both references incorporated herein by reference, for further explanation of the simulated moving bed countercurrent process flow scheme.

Another embodiment of a simulated moving bed flow system suitable for use in the process of the present invention is the co-current high efficiency simulated moving bed process disclosed in our assignee's U.S. Pat. No. 4,402,832, incorporated by reference herein in its entirety.

It is contemplated with any flow scheme used to carry out the present invention that at least a portion of the extract output stream will pass into a separation means wherein at least a portion of the desorbent material can be separated to produce an extract product containing a reduced concentration of desorbent material. Preferably, but not necessary to the operation of the process, at least a portion of the raffinate output stream will also be passed to a separation means wherein at least a portion of the desorbent material can be separated to produce a desorbent material stream which can be reused in the process and a raffinate product containing a reduced concentration of desorbent material. The separation means will typically be a fractionation column, the design and operation of which is well-known to the separation art.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor-phase operation. Desorption conditions will thus include, as hereinbefore mentioned, a pressure sufficient to maintain liquid-phase. Adsorption conditions will include the same range of temperatures and pressures as used for desorption conditions.

A static test procedure and apparatus may be employed to test various adsorbents with a particular feed mixture to determine the relative retention by the adsorbent of each component of the mixture. The procedure involves mixing together equal quantities of each component, the relative retention of which is to be determined, and a convenient solvent or desorbent material. A desorbent is selected that will have a boiling point well separated from those of the isomers being tested. The resulting solution is then placed in a vessel with a quantity of the appropriate adsorbent and is allowed to remain, with occasional stirring, for about 24 hours. The solution is then analyzed for each component and the relative retention thereof is determined in terms of the ratio, R, of the less strongly adsorbed component to the more strongly adsorbed component, the relative retention of the more strongly adsorbed component by the adsorbent being greater, the higher the above ratio.

A dynamic testing apparatus is employed to test various adsorbents with a particular feed mixture and desorbent material to measure the adsorption characteristics of retention capacity and exchange rate. The apparatus consists of a helical adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect quantitatively or determine qualitatively one or more components in the effluent stream leaving the adsorbent chamber. A pulse test, performed using this apparatus and the following general procedure, is used to determine data for various adsorbent systems. The adsorbent is filled to equilibrium with a particular desorbent material by passing the desorbent material through the adsorbent chamber. At a convenient time, a pulse of feed containing known concentrations of a tracer and of a particular extract component or of a raffinate component or both, all diluted in desorbent material is injected for a duration of several minutes. Desorbent material flow is resumed, and the tracer and the extract component or the raffinate component (or both) are eluted as in a liquid-solid chromatographic operation. The effluent can be analyzed on-stream or alternatively, effluent samples can be collected periodically and later analyzed separately by analytical equipment and traces of the envelopes or corresponding component peaks developed.

From information derived from the test, adsorbent performance can be rated in terms of void volume, retention volume for an extract or a raffinate component, and the rate of desorption of an extract component from the adsorbent. The retention volume of an extract or a raffinate component may be characterized by the distance between the center of the peak envelope of an extract or raffinate component and the center of the peak envelope of the tracer component or some other known reference point. It is expressed in terms of the volume in cubic centimeters of desorbent material pumped during this time interval represented by the distance between the peak envelopes. The rate of exchange of an extract component with the desorbent material can generally be characterized by the width of the peak envelopes at half intensity. The narrower the peak width, the faster the desorption rate. The desorption rate can also be characterized by the distance between the center of the tracer peak envelope and the disappearance of an extract component which has just been desorbed. This distance is again the volume of desorbent material pumped during this time interval.

The following non-limiting examples are presented to illustrate the process of the present invention and are not intended to unduly restrict the scope of the claims attached hereto.

EXAMPLE 1

A number of static tests were performed as described hereinabove to demonstrate that it was possible to separate the isomers by an adsorptive process. A stock solution of dinitrotoluene (DNT) isomers as follows was used in the tests:

| | |
|---|---|
| 2,4-DNT | 0.5 g |
| 2,6-DNT | 0.5 g |
| Mesitylene | 27.3 g |

In the static tests the volume ratio of stock solution to adsorbent was 1.5, except for Ca-X and Na-Y in which it was 2.5. The stock solution and adsorbent were combined in a flask and the amount of each isomer left in the raffinate was determined and the isomer ratio, R=2,6-DNT/2,4-DNT was calculated for a number of adsorbents. The results are as follows:

| Adsorbent | R2,6/2,4-DNT Stock | R2,6/2,4-DNT Raffinate |
|---|---|---|
| BaK—X | 1.04 | 1.67 |
| Ba—Y | 1.04 | 1.49 |
| Ca—Y | 1.04 | 1.70 |
| K—Y | 1.04 | 1.29 |
| Na—X | 1.04 | 1.41 |
| Ca—X | 1.06 | 1.13 |
| K—X | 1.06 | 2.82 |
| Na—Y | 1.06 | 1.29 |

These tests show that 2,4-DNT is selectively adsorbed in each case, hence that, in combination with an appropriate desorbent, these isomers may be separated by our adsorptive process. Several of these adsorbents also underwent the pulse test as described in the next example, confirming the results of the static test.

EXAMPLE 2

The previously described pulse test apparatus was used to obtain data for this example in a series of nine test runs. The liquid temperature was 150° C. and the flow was up the column at the rate of 1.2 ml/min. The feed stream comprised 2.6 cc pulses of a solution containing 0.5 gm of each of the dinitrotoluene isomers, and 0.5 gm of n-$C_{20}$ tracer, all dissolved in 3 gm of desorbent. The column was packed with clay bound adsorbent of 30–60 mesh particle size.

The selectivity (B), as earlier described, was calculated from the trace of the peaks generated for the components. The results of this example are shown on the following Table I and the Figures, numbered to correspond with the Run No.:

TABLE I

| FIG. & Run. No. | Adsorbent | B $\frac{2,4}{2,6}$ | Desorbent |
|---|---|---|---|
| 1 | K—Y | 3.25 | 50% 1-butanol; 50% toluene |
| 2 | Na—Y | 2.1 | 50% n-butanol; 50% toluene |
| 3 | Na—Y | 2.1 | 50% nitrobenzene; 50% toluene |
| 4 | Na—Y | 2.48 | 50% n-pentanol; 50% toluene |
| 5 | Ca—Y | 2.89 | 50% n-pentanol; 50% toluene |
| 6 | BaK—X | 2.66 | 50% n-pentanol; 50% toluene |
| 7 | Li—Y | 2.18 | 50% 1-butanol; 50% toluene |
| 8 | Li—Y | 2.54 | 50% 1-pentanol; 50% toluene |
| 9 | Mg—Y | 2.7 | 50% 1-pentanol; 50% toluene |

In general, the above data does show that the present invention provides a 2,4-dinitrotoluene selective system, with adequate selectivities for the commercial use of the separation of the present invention.

EXAMPLE 3

Figure 10:
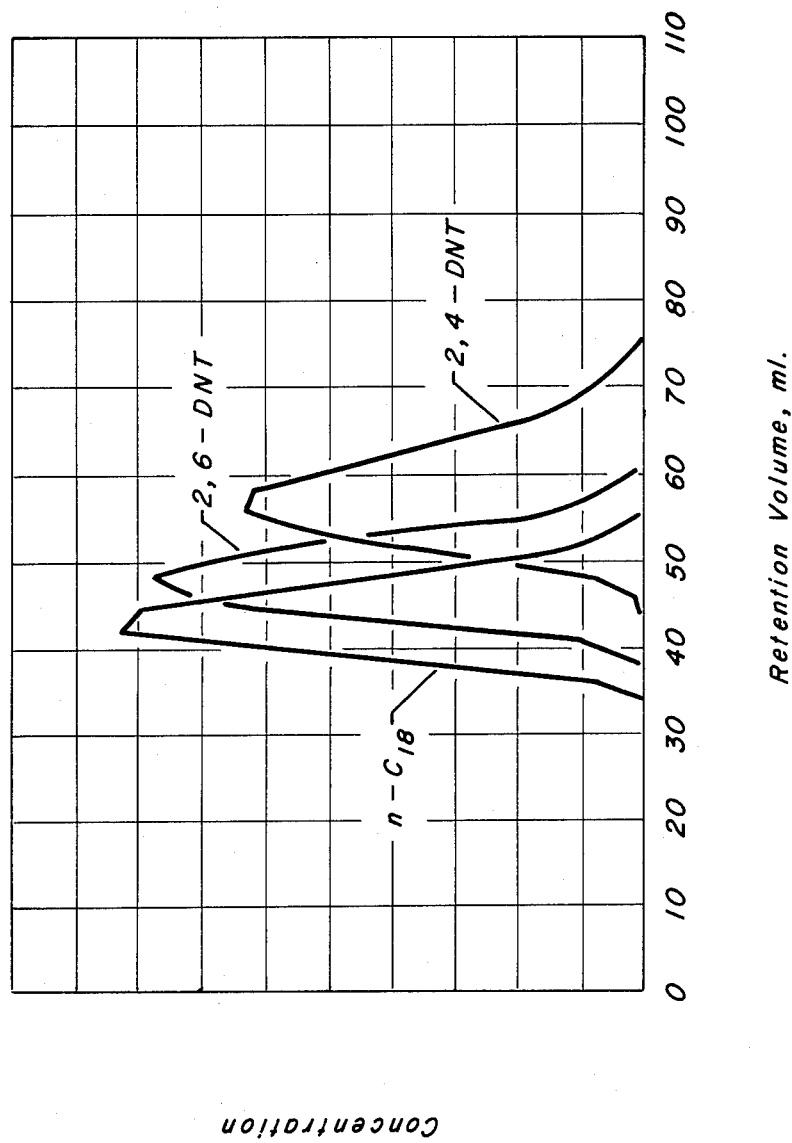
Figure 11:
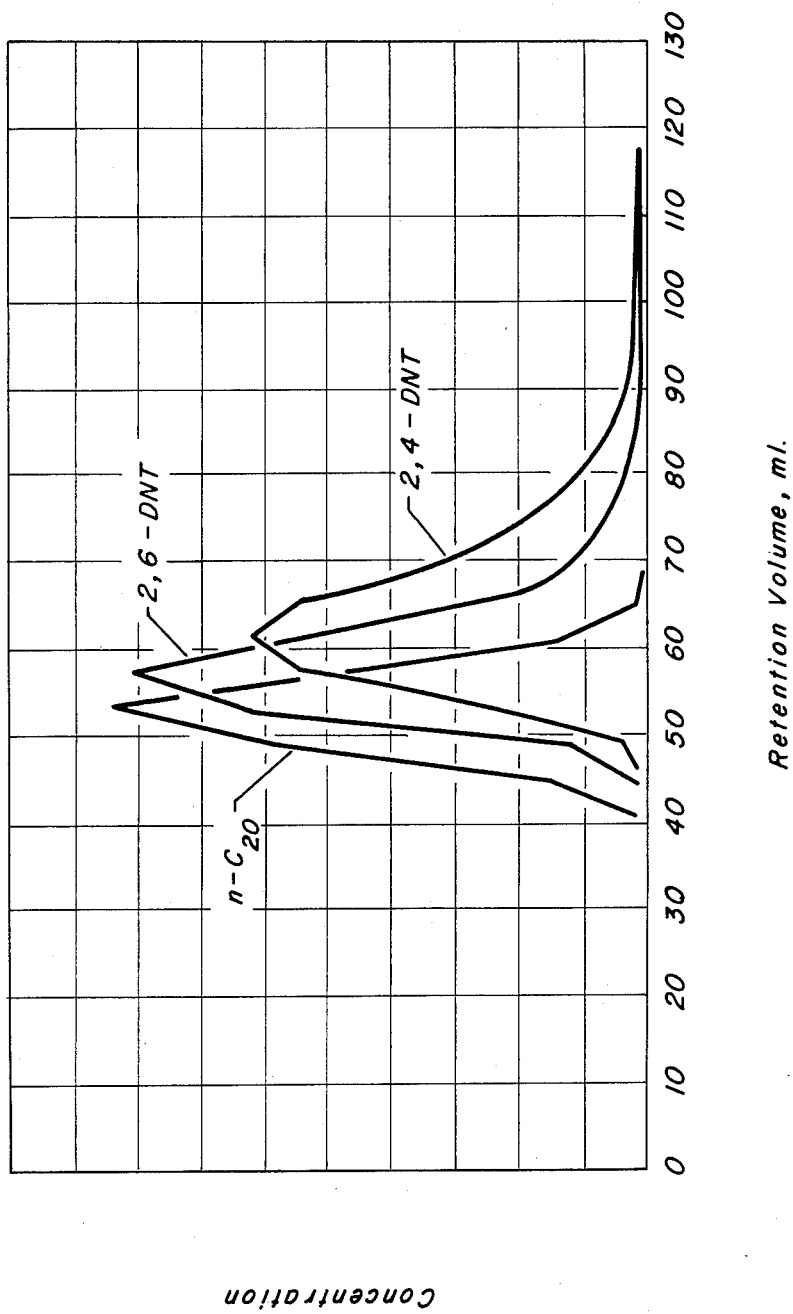
Figure 12:
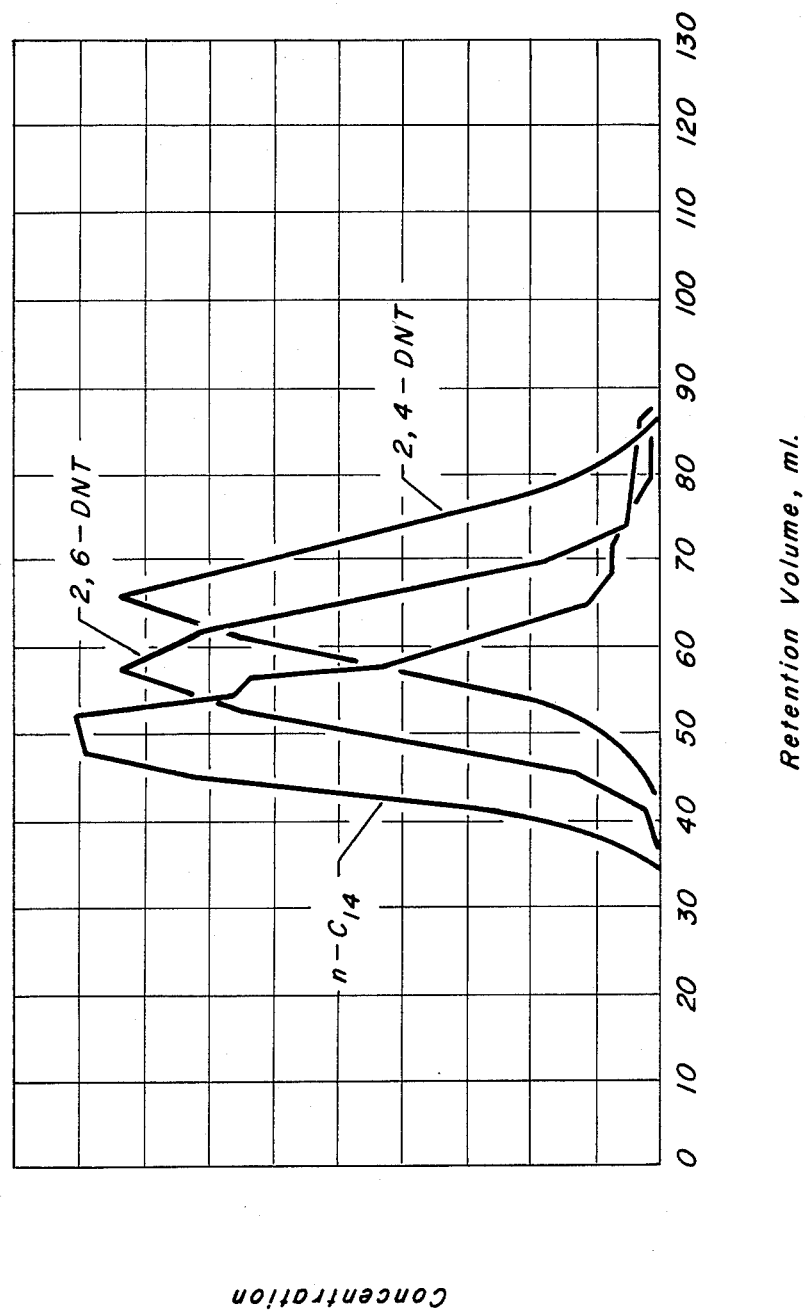
Figure 13:
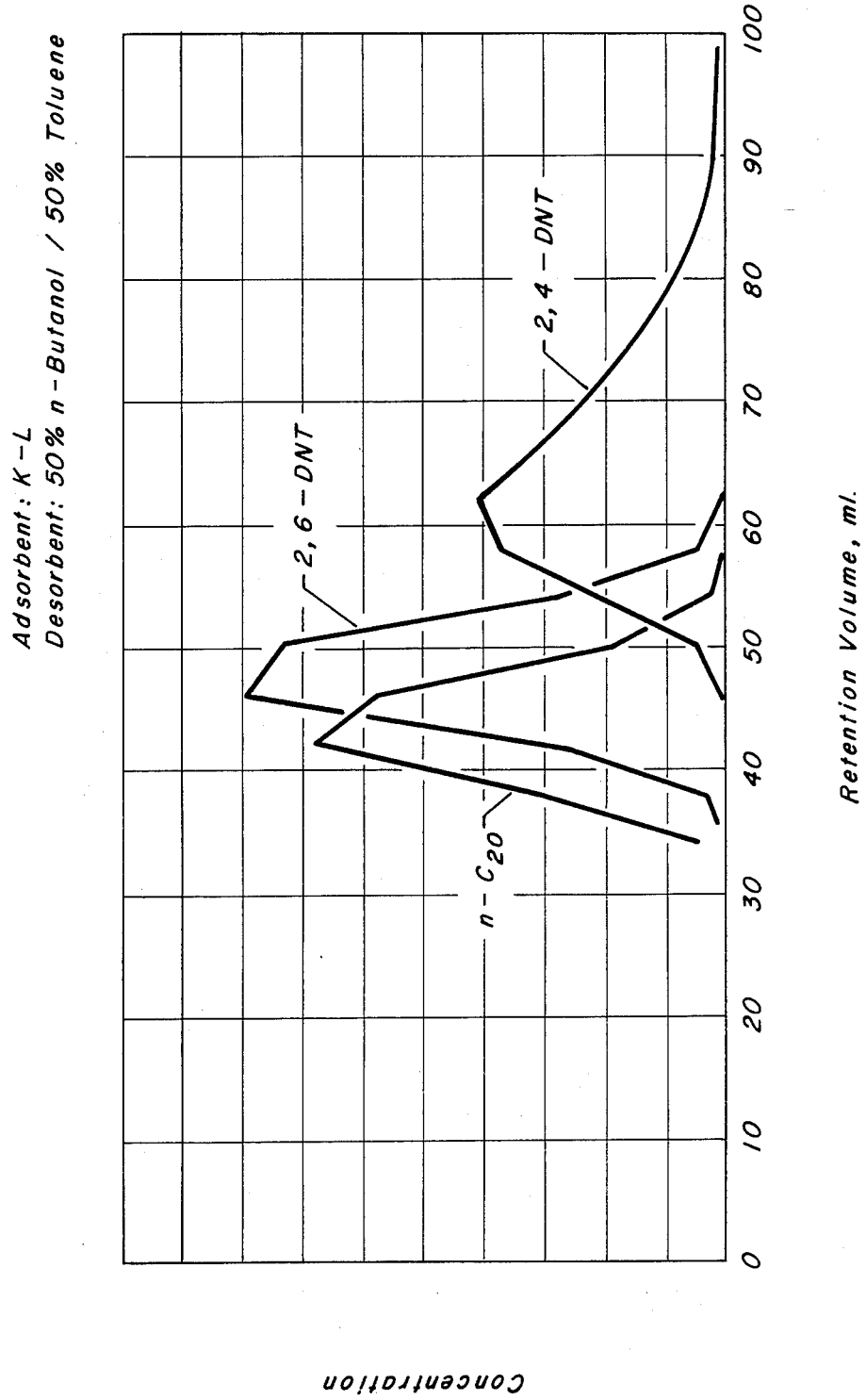

The previously described pulse test was also used to obtain data from runs similar to those of Example 2, but using desorbents other than those exemplified above. In this example, a normal $C_{18}$ or $C_{14}$ hydrocarbon tracer was used in addition to n-$C_{20}$ and either potassium or sodium exchanged Y-type zeolite or a potassium exchanged L-type zeolite. In these tests, the column temperature was 110° C., flow rate up the column was 1.2 ml. per min. and a feed stream pulse of 2.6 cc. was again used. The feed stream contained quantities of additional minor isomers of 2,3-DNT and 3,4-DNT, but their presence does not have any substantial effect on the separation of 2,4- and 2,6-DNT. The results of the pulse test are shown in FIGS. 10 through 13. The values of B2,4/2,6 calculated from the Figures as explained previously are shown in Table II below:

TABLE II

| FIG. No. | Adsorbent | Tracer | B2,4/2,6 | Desorbent |
|---|---|---|---|---|
| 10 | K—Y | n-$C_{18}$ | 3.0 | ethyl acetate |
| 11 | K—L | n-$C_{20}$ | 2.0 | ethyl acetate |
| 12 | Na—Y | n-$C_{14}$ | 2.06 | 2-heptanone |
| 13 | K—L | n-$C_{20}$ | 4.36 | 50% n-butanol 50% toluene |

What is claimed is:

1. A process for separating 2,4-dinitrotoluene from a feed mixture comprising 2,4-dinitrotoluene and 2,6-dinitrotoluene, said process comprising contacting said mixture at a temperature within the range from about 20° C. to about 200° C. and at a pressure to maintain liquid phase with an adsorbent comprising an L type zeolite whose cations have been exchanged with K, an X type zeolite whose cations have been exchanged with a cation selected from the group consisting of Na, Ca, Ba and K, or a Y type zeolite whose cations have been exchanged with a cation selected from the group consisting of Ca, Ba, K, Na, Li and Mg thereby selectively adsorbing said 2,4-dinitrotoluene, removing the remainder of said mixture from said adsorbent, and then recovering said 2,4-dinitrotoluene by desorption at a temperature within the range from about 20° C. to about 200° C. and at a pressure to maintain liquid phase with a desorbent material comprising a $C_3$ to $C_5$ alcohol, a ketone, an ester, or nitrobenzene.

2. The process of claim 1 wherein said process is effected with a simulated moving bed flow system.

3. The process of claim 1 wherein said process is effected with a static bed system.

4. The process of claim 1 wherein said absorbent is selected from the group consisting of X type zeolites whose cations have been exchanged with Ba and Y type zeolites whose cations have been exchanged with a cation from the group consisting of K, Na, Li and Mg.

5. The process of claim 1 wherein said adsorbent is selected from the group of X type zeolites whose cations have been exchanged with a cation from the group consisting of Ba and Na and Y type zeolites whose cations have been exchanged with a cation from the group consisting of Ba, Na, Li and K.

6. The process of claim 1 wherein said desorbent comprises a $C_3$ to $C_5$ alcohol.

7. The process of claim 6 wherein said desorbent additionally contains toluene.

8. The process of claim 1 wherein said absorbent is an L type zeolite and said desorbent is selected from the group consisting of n-butanol and ethyl acetate.

9. The process of claim 8 wherein said desorbent additionally contains toluene.

10. The process of claim 1 wherein said absorbent is an X type zeolite and said desorbent comprises pentanol.

11. The process of claim 10 wherein said desorbent additionally contains toluene.

12. The process of claim 1 wherein said absorbent is a Y type zeolite and said desorbent comprises a $C_3$ to $C_5$ alcohol.

* * * * *